United States Patent [19]

Foley

[11] 4,456,722

[45] Jun. 26, 1984

[54] COMPOSITION FOR CONTROL OF BACTERIA AND VIRUSES

[76] Inventor: Lary L. Foley, 4443 - 20th St., San Francisco, Calif. 94114

[21] Appl. No.: 440,395

[22] Filed: Nov. 9, 1982

[51] Int. Cl.$^3$ .................. C08G 65/32; C08L 71/02
[52] U.S. Cl. ................... 524/413; 524/612; 525/405; 525/409; 544/185
[58] Field of Search ............... 524/413, 612; 525/405, 525/409; 544/185

[56] References Cited

U.S. PATENT DOCUMENTS

| | | | |
|---|---|---|---|
| 3,067,089 | 12/1962 | Winslow et al. | 167/17 |
| 3,085,081 | 4/1963 | Bailey, Jr. | 260/42 |
| 3,125,544 | 3/1964 | Winslow et al. | 260/43 |
| 3,164,560 | 1/1965 | Suter | 269/6 |
| 3,227,652 | 1/1966 | Ackerman | 252/49.5 |
| 3,228,829 | 1/1966 | Wolf et al. | 167/33 |
| 3,312,588 | 4/1967 | Larson | 167/33 |
| 3,355,400 | 11/1967 | Smith et al. | 260/17.5 |
| 3,387,061 | 6/1968 | Smith et al. | 260/874 |
| 3,514,288 | 5/1970 | Silver | 96/33 |
| 3,925,216 | 12/1975 | Moorhouse | 252/49.3 |
| 3,928,607 | 12/1975 | Luloff et al. | 424/249 |
| 4,170,673 | 10/1979 | Conti | 427/401 |
| 4,171,337 | 10/1979 | Rosen et al. | 264/56 |

OTHER PUBLICATIONS

"POLYOX Water-Soluble Resins are Unique," pp. 5–19 and 2 unnumbered pages.
"DOWICIL 200 Preservative for Cosmetics," Dow Chemical Company publication, 1980, pp. 3–9, 2 of 7 thru 7 of 7, 4 unnumbered pages and cover page.

*Primary Examiner*—Earl A. Nielsen
*Attorney, Agent, or Firm*—Townsend and Townsend

[57] ABSTRACT

A novel association complex in disclosed, formed by the interaction between a hexamethylenetetramine quaternary salt of a halogenated allyl halide and a water-soluble homopolymer of ethylene oxide. The composition is neutral in pH, fluoresces at a characteristic wavelength of 355 nanometers, has unusual moisture retention characteristics, and possesses the unique ability to inhibit viral replication. The composition is preferably used in aqueous solution, and finds utility as a protective moisturizing agent for the skin, as a healing agent for skin injuries, as a germicidal lubricant, and as a medication for topical application to lesions due to viral infections.

7 Claims, No Drawings

COMPOSITION FOR CONTROL OF BACTERIA AND VIRUSES

BACKGROUND OF THE INVENTION

1. Field of the Invention

This invention relates to novel compositions, and particularly to novel association complexes suitable for human use which combine specific tissue affinity with the ability to control both bacterial growth and viral replication.

The spread of viral infections has increased dramatically in recent years, notable examples being the proliferation of herpes simplex viruses, which have replaced syphilis and gonorrhea as the most prevalent venereal disease in the United States. As with most viral infections, there is no known cure for herpes. Although some persons are less susceptible to viral infection than others, there is presently available no reliable means for inhibiting replication of viruses after infection has occurred.

It is therefore an object of the present invention to provide a novel composition capable of inhibiting viral replication, and further capable of a wide variety of protective uses against other diseaseproducing organisms. Other objects and advantages will be apparent from the following description.

2. Description of the Prior Art

Germicidal compounds of the type used to form the present association complex are disclosed in Wolf et al., U.S. Pat. No. 3,228,829, and Larsen, U.S. Pat. No. 3,312,588. Such materials are known to be useful as preservatives and germicidal agents when appropriately formulated. One example of such a compound is commercially available from the Dow Chemical Company, Midland, Mich., under the trademark DOWICIL ® 200.

Water-soluble polymers of the type used to form the present association complex are available from Union Carbide Corporation, Danbury, Connecticut in various grades under the trademark POLYOX ®. Such materials function, among other things, as lubricants in a variety of applications. Descriptions of such applications are found in Ackerman, U.S. Pat. No. 3,227,652 (Jan. 4, 1966), Moorhouse, U.S. Pat. No. 3,925,216 (Dec. 9, 1975), Conti, U.S. Pat. No. 4,170,673 (Oct. 9, 1979) and Rosen, et al., U.S. Pat. No. 4,171,337 (Oct. 16, 1979).

SUMMARY OF THE INVENTION

A novel association complex is provided, formed by the combination of a hexamethylenetetramine quaternary salt of a halogenated allyl halide and a water-soluble homopolymer of ethylene oxide. While its components are individually alkaline, the association complex is substantially neutral in aqueous solution, and is substantive to certain types of proteins. Due to this substantivity, the complex possesses an unusual ability to form a thin film with softening and smoothing properties when applied to the skin. In one particularly unexpected application, the complex can be applied to herpetic lesions, with the result that the lesion cycle is disrupted, leading to shortening of duration or, in some cases, a dramatic remission of all symptoms. In general, the novel association complex has demonstrated utility in both germicidal applications and the inhibition of viral replication, in addition to a variety of uses due to its protective film-forming ability—i.e., as a local analgesic for sunburned or abraded skin, for hastening wound healing and treating first and second degree burns, and as a lubricating and moisturizing agent for a wide variety of both therapeutic and nontherapeutic uses.

DESCRIPTION OF THE PREFERRED EMBODIMENTS

The association complex of the present invention is prepared by combining the following two components: (1) a hexamethylenetetramine quaternary salt of a halogenated allyl halide, and, (2) a water-soluble homopolymer of ethylene oxide. The result is a novel chemical species, distinct from either of the two starting materials in both chemical structure and physical and chemical properties, and fluorescing at a characteristic excitation wavelength of 355 nanometers. The starting materials are described in more detail below.

The halogenated allyl halides which form the quaternary salts with hexamethylenetetramine generally have the formula:

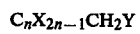

where n is 2 or 3, each X is independently hydrogen or halogen, provided that at least one X is halogen, and Y is halogen. The halogens are preferably all the same, and, more preferably, selected from the group consisting of chlorine, bromine or iodine. Chlorine and bromine are particularly preferred. Examples of such halogenated compounds are 2,3-dibromopropene, 1,3-dichloropropene, 1,1,2-trichloro-3-iodopropene, 1,1,3-trichloropropene, 1,1,2,3-tetrabromopropene, 1,2,3-trichloropropene, 3-bromo-1-chloro-2-fluoropropene, 3-bromo-2-(bromomethyl)-propene, 1,4-dichloro-2-butene, 2-(chloromethyl)-3,3,3-trifluoropropene and 4-chloro-1,1,1-trifluoro-2-butene. The quaternary salts themselves are ordinarily formed by the union of one molecule each of hexamethylenetetramine and organic halide, but in some cases, two or more molecules of hexamethylenetetramine are involved per molecule of halide.

Any water-soluble homopolymer of ethylene oxide in which the repeating unit is —O—CH$_2$—CH$_2$— will be suitable for use in the present composition. Preferred such polymers are those having a molecular weight of about 100,000 or more. Particularly preferred are those having a molecular weight ranging from about 100,000 to about 6,000,000, the most preferred ranging from about 1,000,000 to about 5,000,000.

The relative quantities of these two reactants are not critical and can vary over a wide range, while still producing an association complex having the desired properties. For most applications a (quaternary salt):(ethylene oxide polymer) weight ratio of from about 1:0.1 to about 1:50, preferably about 1:1 to about 1:20, most preferably from about 1:2 to about 1:8, will provide the best results.

It should be understood that the composition of the present invention is contemplated to include the above-described complex as well as mixtures of the complex with the quaternary salt and/or the ethylene oxide polymer in uncomplexed form.

In its preferred form, the complex is dissolved in water to produce a homogeneous viscous solution of uniform consistency. The concentration is not critical and will vary with the particular reactants used to form the complex, their relative amounts, the grades of the reactants and the particular application for which the complex is formulated. For most applications, an overall concentration ranging from about 0.1% to about 10% by weight, preferably from about 0.5% to about 5.0% by weight, will provide the best results.

The complex or its aqueous solution can be prepared by any conventional manner, provided that rupture of the polymer chains is substantially avoided to retain the desired viscosity, and further provided that a final composition or solution of uniform viscosity and consistency results. Preferably, the quaternary salt is first dissolved in water and the ethylene oxide polymer is then added. Prior to addition of the polymer, it is preferable to permit the quaternary salt to equilibrate in solution. During equilibration, the quaternary salt solution drifts from an initial pH of approximately 5.0 to an alkaline pH of approximately 8.0 to 8.5.

An aqueous solution of the polymer is then prepared in a variety of ways. One method involves first suspending the polymer in a water-miscible organic liquid in which the polymer itself is insoluble. The suspension is subsequently combined with water. This provides a uniform solution by overcoming the high affinity of the polymer for water. A second method is the addition of the polymer in powdered form to boiling water, in which the resin is insoluble. The resulting dispersion is then cooled to provide a uniform solution. A third and particularly effective method involves the sifting of the polymer in powdered form onto a rapidly moving sheet of water to avoid aggregation of the polymer before it dissolves. In general, any method of achieving and maintaining a fine dispersion of polymer particles while dissolution is taking place will suffice. Failure to maintain such a dispersion frequently results in the formation of a hard gel consisting of an outer shell formed by the hydrogen bonding of water molecules to the polymer, and an interior containing dry, unwetted polymer.

Additional materials may be mixed with the complex or dissolved in the aqueous solution on an optional basis for a variety of purposes, depending on the actual quaternary salt or polymer used, and the amounts and the intended use of the composition. Examples of such additives include stabilizers against oxidation and viscosity decay, particularly alcohols, glycols and manganous ion. Further examples include complexing agents as well as inert materials, selected to adapt the composition to its various uses. These are more fully described below.

The composition of the present invention is useful for topical application and, provided that there is no free unassociated quaternary salt included, for systemic application as well.

In topical application, the complex is effective in supplying a protective moisturizing layer. It is thus useful for suppressing wrinkles and generally moisturizing skin without an oily or viscous sensation. This property, when combined with the germicidal activity of the complex, renders the complex particularly useful in lubricating applications where bacterial or viral infections frequently occur. As one example, the complex is an effective lubricant for catheter insertion, resulting in the avoidance of infections which frequently accompany such procedures. A further example is the use of the composition as a sexual lubricant. The neutral pH of the composition provides a non-irritating, soothing and lubricating effect, while the germicidal activity aids in the prevention of sexually transmitted diseases and ailments commonly associated with sexual contact. The composition thus provides an effective way of achieving lubrication, while preventing urethritis, viral infections, such as Herpes simplex, and sexually communicated microorganisms, such as gonorrhea.

The complex further possesses the unusual ability to inhibit viral replication, rendering it particularly useful in the control of viral diseases. The complex can be directly applied to external skin lesions caused by Herpes Simplex Hominis (Type 1) and Herpes Simplex Genitalis (Type 2), with the effect of hastening, often dramatically, disappearance of the lesions. The complex is likewise effective in preventing the spread of the virus from one person to another.

The complex can be formulated by techniques known in the art relative to poly(ethylene oxide) polymers to impart substantivity to specific types of proteins, rendering it useful for both topical and systemic applications where specificity is sought. Examples of tissues which can be specifically targeted are pulmonary tissue, epithelium, basal epithelium, and nasopharyngeal mucosa, and, on a more general level, myosin, collagens, keratins, etc. The polymer chain itself can be modifed by the attachment of appropriate prosthetic groups, also known in the art, to enhance its binding affinity to particular proteins. Its germicidal and viral inhibition properties can thus be directed at specific sites in or on the human body.

The following examples are offered by way of illustration and are intended neither to limit nor define the invention in any manner.

EXAMPLE 1

A solution was prepared by dissolving DOWICIL 200, an antimicrobial cosmetics preservative obtainable from The Dow Chemical Company, Midland, Michigan, in water to provide a 0.2% solution by weight. The preservative is an off-white powder, containing as the active ingredient the cis-isomer of 1-(3-chloroallyl)-3,5,7-triaza-1-azoniaadamantane chloride, the latter constituting 94% by weight of the powder. The pH of the fresh solution was within the range of 4–6. The solution was then permitted to stand for approximately 24 hours, by which time equilibrium was reached and the final pH was approximately 8.0–8.5.

To the above solution was added sufficient POLYOX (coagulant grade), a poly(ethylene oxide) resin obtainable from Union Carbide Corporation, Danbury, Connecticut, to provide a solution containing 0.8% by weight of the resin in addition to 0.2% by weight of the preservative. POLYOX is defined by its supplier as a thermoplastic poly(ethylene oxide) polymer in white powder form, the coagulant grade having an average molecular weight of approximately 5,000,000. To combine the resin and the DOWICIL solution, the latter was fed by a centrifugal pump to a tray-like trough as a fastmoving thin sheet of liquid. The POLYOX resin was fed to the liquid sheet by a hopper positioned above the trough, the hopper terminating in a thin slit which provided a controlled flow of fine powder to the liquid. The trough contents were delivered to a stirred vat where they were stirred until the particles dissolved. A trace of manganous ion, approximately 0.0004% by weight as the sulfate, was added as an oxidation inhibitor.

The mixture thus formed had a pH of about 9.0, and was of the consistency and color of coarse oatmeal. The mixture was then permitted to stand for a period of about three weeks. During this time, the pH dropped from its initial value of about 9.0 to about 7.1, and the solution assumed a smooth and silky consistency, turning clear. Upon further standing, the pH dropped to about 6.8, and the color turned to a brilliant yellow-green. Measurements of pH were obtained using a Corning 125 glass combination electrode with a buffer reference standard. The composition was further measured for fluorescence on a Perkin-Elmer LS-5 Fluorescence Spectrophotometer, whereupon it was found to fluoresce at an excitation wavelength of 355 nanometers, a property absent in the solutions of each of the two reactants taken individually.

EXAMPLE 2

The following experiment was conducted to demonstrate the ability of the complex of the present invention to inhibit viral replication.

The composition prepared in Example 1 was combined with an undiluted stock of a strain of Herpes Simplex Virus (Type 2), the latter having an infectivity of approximately 10,000 $ID_{50}$ per ml, at a volumetric ratio of 10:1 (composition:virus stock). The mixture was then incubated at room temperature for twenty miutes. Saline dilutions of the mixture were then prepared, at mixture:saline volumetric ratios of 1:5, 1:10, and 1:20, and inoculated into Vero cell cultures, 0.2 ml per culture tube. After 24 hours' incubation, the cultures were examined and stained. The culture inoculated with 1:5 dilution showed inhibition of virus replication.

EXAMPLE 3

The composition prepared in Example 1 was used by ten male prostitutes who claim anal intercourse approximately daily with a frequency of up to five times per day. Prior to use of the composition, each of the subjects experienced frequent non-specific urethritis and gonorrhea. For test periods lasting from approximately two months to approximately ten months of continued use, the subjects each applied the combination to their genitalia and to those of their partners for use as a lubricant during anal intercourse. During the test periods, none of the subjects contracted either urethritis or gonorrhea and none experienced irritation as a result of using the composition.

EXAMPLE 4

The composition prepared in Example 1 was used by a licensed physician for administration to patients as a lubricant for catheter insertion. The composition was used on approximately 50 patients over a period of approximately three months. The incidence of infections associated with urethral catheter insertion, which normally occur in about 80% of such insertions, was effectively reduced to zero.

EXAMPLE 5

The composition prepared in Example 1 was distributed to a group of eighteen people suffering from Herpes Simplex (Type 1) virus infections and experiencing the appearance of typical labial and skin lesions commonly associated with the virus. Upon direct application three to four times daily of the composition to the lesions, the subjects noticed an abrupt disruption of the typical progress of disease leading to rapid disappearance of the lesions.

EXAMPLE 6

The composition prepared in Example 1 was supplied to two subjects suffering from the dermal manifestations of Herpes Zoster (biologically and antigenically different from Herpes Simplex types 1 and 2). The composition was applied to the affected areas (commonly known as "shingles") 3 to 4 times daily. In each case, while the deeper portions of the lesions underlying the skin remained unaffected, within two days in each case there was dramatic cessation of cutaneous pain and skin eruption. This suggests that such compositions may have wide application in viral infections generally, when appropriately compounded.

EXAMPLE 7

The composition prepared in Example 1 was applied as a thin layer to facial skin. The result was a perceived smoothing of wrinkles and general softening of skin, inferred to be due to increased moisturization of the stratum corneum, coupled with a subjective impression of skin well-being and improved tone.

For comparison, a similar experiment was conducted using a solution of POLYOX alone. While a moisturizing effect was initially observed, the composition soon began to dry out, resulting in flaking and peeling, separating the composition layer from the skin.

EXAMPLE 8

A series of compositions similar to that of Example 1 was prepared. The DOWICIL content of the compositions was varied from zero to 1.0% by weight at increments of 0.2%, while all other components (POLYOX, manganous sulfate and water) were held constant at the levels stated in Example 1. Small diameter disks of filter paper were then saturated with the compositions.

Plates of nutrient agar were streaked with one of six bacterial cultures and the saturated disks were then placed on the streaked surface. The growth media were then incubated under optimal growth conditions for periods of time sufficient to permit observable growth of the organisms. This varied from one organism to the next, ranging from one to several days. The media were then observed for the degree of growth surrounding each filter paper disk and the organisms were characterized as "sensitive" (total absence of growth in area surrounding disk), "resistant" (little or no growth inhibition in area surrounding disk) and "intermediate." The results are listed below.

| AGAR INHIBITION TEST RESULTS Composition: POLYOX - 0.8% (by weight); DOWICIL - as shown; water - balance | | | | | | | |
|---|---|---|---|---|---|---|---|
| | Wt. % | Growth Characteristics* | | | | | |
| Organism | DOWICIL: | 0 | 0.2% | 0.4% | 0.6% | 0.8% | 1.0% |
| Neisseria gonorrhoeae | | R | S | S | S | S | S |
| E. Coli | | R | I | S | S | S | S |
| Pseudomonas Spp. | | R | R | R | I | S | S |
| Staph Aureus | | R | S | S | S | S | S |
| Beta Streptococcus Group A | | R | S | S | S | S | S |
| Candida Albicans (Monilia) | | R | R | R | R | R | R |

*S: Sensitive
R: Resistant
I: Intermediate

When compared with published data from similar agar inhibition tests using DOWICIL alone ("DOWICIL 200 PRESERVATIVE FOR COSMETICS," publication of The Dow Chemical Company, 1980, Form No. 192-753-80, page 3), where concentrations resulting in growth inhibition ranged from 50 ppm to 400 ppm, it is clear that the toxicity of the DOWICIL in the above composition is lessened by its inability to diffuse through the growth medium in its complexed form with POLYOX polymer. The *E. coli* and Pseudomonas data offer direct comparisons, since they compare with 100 ppm and 400 ppm concentrations in the published DOWICIL data.

The foregoing description is offered solely for purposes of illustration; the invention is not intended to be limited to the particular features described. Numerous modifications and variations of the above still falling within the spirit and scope of the invention as claimed hereinbelow will be readily apparent to those skilled in the art.

What is claimed is:

1. An association complex formed by the combination of a hexamethylenetetramine quaternary salt of a halogenated allyl halide and a water-soluble homopolymer of ethylene oxide.

2. An aqueous solution of a complex according to claim 1 in which said halogenated allyl halide has the formula $$C_nX_{2n-1}CH_2Y$$

where n is 2 or 3, each X is independently hydrogen or halogen with the proviso that at least one X is halogen, and Y is halogen; and said homopolymer of ethylene oxide has an average molecular weight of at least about 100,000.

3. An aqueous solution of a complex according to claim 1 in which said halogenated allyl halide has the formula $$C_nX_{2n-1}CH_2Y$$

where n is 2 or 3, each X is independently selected from the group consisting of hydrogen, chlorine, bromine or iodine, with the proviso that at least one X is selected from the group consisting of chlorine, bromine, or iodine; and said homopolymer of ethylene oxide has an average molecular weight of from about 100,000 to about 6,000,000.

4. A complex according to claim 1 in which the weight ratio of said quaternary salt to said homopolymer is from about 1:0.1 to about 1:50.

5. A solution according to claim 3 in which the weight ratio of said quaternary salt to said homopolymer in said complex is from about 1:1 to about 1:20, and the concentration of said complex in said solution is from about 0.1% to about 10% by weight.

6. An aqueous solution of a complex according to claim 1 in which said halogenated allyl halide is 1,3-dichloropropene, said homopolymer of ethylene oxide has an average molecular weight ranging from about 1,000,000 to about 5,000,000, the weight ratio of said quaternary salt to said homopolymer in said complex is from about 1:2 to about 1:8, and the concentration of said complex in said solution is from about 0.5 to about 5.0% by weight.

7. A solution according to claim 6 further comprising a stabilizing amount of manganous ion.

* * * * *